United States Patent
Thirumalai et al.

(10) Patent No.: US 8,303,937 B2
(45) Date of Patent: Nov. 6, 2012

(54) DENDRITIC POLYMERS AND MAGNETIC RESONANCE IMAGING CONTRAST AGENT EMPLOYING THE SAME

(75) Inventors: Dhakshanamurthy Thirumalai, Hsinchu (TW); Chin-I Lin, Yongkang (TW); Shian-Jy Wang, Hsinchu County (TW)

(73) Assignee: Industrial Technology Research Institute (TW)

( * ) Notice: Subject to any disclaimer, the term of this patent is extended or adjusted under 35 U.S.C. 154(b) by 902 days.

(21) Appl. No.: 12/174,439

(22) Filed: Jul. 16, 2008

(65) Prior Publication Data

US 2009/0169481 A1 Jul. 2, 2009

(30) Foreign Application Priority Data

Dec. 31, 2007 (TW) .............................. 96151449 A

(51) Int. Cl.
  C08L 73/00 (2006.01)
  A61K 9/00 (2006.01)
  C07D 407/00 (2006.01)
(52) U.S. Cl. ........ 424/9.3; 424/1.11; 424/1.65; 424/9.1; 424/9.32; 424/9.34; 424/9.36; 424/9.361; 424/9.364; 424/DIG. 16; 525/25; 525/26; 525/27; 525/28; 525/33; 525/37
(58) Field of Classification Search .............. 528/25, 528/26, 27, 28, 33, 37; 424/1.11, 1.65, 9.1, 424/9.3, 9.32, 9.34, 9.36, 9.361, 9.364, DIG. 16
See application file for complete search history.

(56) References Cited

U.S. PATENT DOCUMENTS

| 5,834,020 A | * | 11/1998 | Margerum et al. | ............ 424/484 |
| 7,745,547 B1 | * | 6/2010 | Auerbach et al. | ............. 525/409 |
| 2002/0123609 A1 | | 9/2002 | Frechet et al. | |

FOREIGN PATENT DOCUMENTS

| JP | 9512264 | 12/1997 |
| JP | 2004-307356 | 11/2004 |
| JP | 2006-188683 | 7/2006 |
| TW | 200724163 | 7/2007 |

OTHER PUBLICATIONS

Jaffres, Paul-Alain, et al., "Synthesis of Highly Fuctionalised Dendrimers Based on Polyhedral Silsequioxane Cores", J. Chem. Soc., Dalton Trans., 1998, pp. 2767-2770, XP-002262722.
Comanita, B., et al., "Star Poly(ethylene oxide)s from Carbosilane Dendrimers", American Chemical Society, 1999, Macromolecules 1999, 32, pp. 1069-1072, XP-000802471.
Chauhan, Bhanu P. S., et al., "Inorganic/Organic Hybrid Nanoreactors Based on Cylic and Cubic Siloxane Scaffolds", Macromolecules, vol. 28, No. 15, Jul. 26, 2005, pp. 6231-6235, XP-00819388.
Office Action dated Aug. 30, 2011 from corresponding Taiwan Application No. 97147621.

* cited by examiner

*Primary Examiner* — Ana Woodward
(74) *Attorney, Agent, or Firm* — Lowe Hauptman Ham & Berner, LLP

(57) ABSTRACT

A dendritic polymer and a magnetic resonance imaging contrast agent employing the same. The magnetic resonance contrast agent includes the dendritic polymer according to the structure of S—(P-D—(Z-L)$_i$)$_j$ or S—(P-D—(X-Z-L)$_i$)$_j$, wherein, S is cyclosilane moiety with j silicon oxygen residual groups, and j is not less than 2; P is

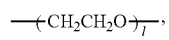

and l is not less than 1; D is a $C_{3-30}$ dendritic moiety having n oxygen residue, and n is not less than 3; X is $C_{3-30}$ moiety having bi-functional groups; Z is a $C_{3-20}$ moiety having a plurality of functional group; and L is a metal cation.

6 Claims, No Drawings

DENDRITIC POLYMERS AND MAGNETIC RESONANCE IMAGING CONTRAST AGENT EMPLOYING THE SAME

CROSS REFERENCE TO RELATED APPLICATIONS

This application is based upon and claims the benefit of priority from the prior Taiwan Patent Application No. 96151449, filed on Dec. 31, 2007, the entire contents of which are incorporated herein by reference.

BACKGROUND OF THE INVENTION

1. Field of the Invention

The invention relates to a dendritic polymer, and more particularly to a magnetic resonance imaging contrast agent containing the dendritic polymer.

2. Description of the Related Art

Currently, medical imaging is capable of creating functional and anatomical images via physical signals of magnetic, photo (fluorescence, near-infrared, X-ray), and radioactive rays emitted by different imaging instruments. The imaging instruments include the Planar X-ray Imaging system, the X-ray Computerised Tomography (CT) system, and the Magnetic Resonance Imaging (MRI) system, which are utilized in the diagnosis of the central nervous system, skeletal nervous system, stomach, ribcage, and angiography, diagnosis of the biliary tractphotography, and the diagnosis of the mutation of tumor tissue. While the appearance of the anatomic tissue does not change, changes in blood circulation, cell activity, and metabolism of the diagnosed location do occur for many different clinical symptoms. Therefore, early detection of the location of illnesses can be accomplished by a highly sensitive Nuclear Imaging system.

Diethylenetriaminepentaacetic acid (DTPA) ligands are widely used in fundamental research as useful chelators in magnetic resonance imaging. The complexes reduce longitudinal and transverse relaxation times ($T_1$ and $T_2$ respectively) of water molecule protons, resulting in a pronounced contrast enhancement in a magnetic resonance image.

However, clinically used contrast agents such as Magnevist (gadolinium salt of DTPA) reveal a disadvantage. Immediately after intravenous application, Magnevist produced images clear quickly from the body through the glomerulus of the kidney and leakage from the vessels due to its low molecular weight compound. With the rapid clearance rate, physicians have limited time and ability to complete time-dependent imaging studies or obtain highly resolved images of patients. Meanwhile, low concentrations of small molecular contrast agents are unable to detect anomalies smaller than a few centimeters when using magnetic resonance imaging (MRI), thereby requiring high concentrations of the contrast agent.

Nevertheless, by using high concentrations, not only does the risk of toxicity caused by the highly concentrated heavy metal occur, but an abundance of molecular imaging agents will also abundantly accumulate. Thus, clinical applications are limited.

Accordingly, a significant topic of research in magnetic resonance imaging technology has been to develop a magnetic resonance imaging agent that efficiently targets the location of the illness by using lower magnetic resonance imaging agent dosages.

Thus, a high-molecular weight magnetic resonance imaging agent with multiple chelates has been developed to overcome the disadvantages such as the rapid clearance rate of the agent from the body and the need for high local small molecular contrast agent concentrations.

BRIEF SUMMARY OF THE INVENTION

The invention provides a dendritic polymer and a magnetic resonance imaging contrast agent, employing the dendritic polymer, capable of recognizing an affected part of a human body with high sensitivity. A detailed description is given in the following embodiments with reference to the accompanying drawings.

An embodiment of a dendritic polymer according to the structure of formula (I) or formula (II) is provided

   formula (I)

   formula (II)

wherein S is cyclosiloxane moiety with j silicon oxygen residual groups, and j is not less than 2. For example, S can be 2,4,6,8,10-pentamethylcyclopentasiloxane.

P is

and l is not less than 1, and P respectively bonds with S by the silicon oxygen residual groups.

D is independent and comprises a $C_{3-30}$ dendritic moiety having n oxygen residue, and n is not less than 3, and D respectively bonds with P and Z by the oxygen residual groups.

X is a $C_{3-30}$ moiety having bi-functional groups, such as

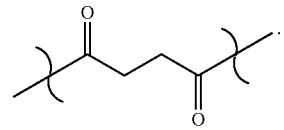

Z is independent and comprises a $C_{3-20}$ moiety having a plurality of functional group, wherein the functional groups are selected from a group consisting of carbonyl, carboxyl, amine, ester, amide, or chelate group, and Z respectively bonds with D and L by the individual functional group. For example, Z is

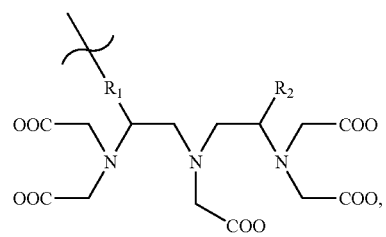

wherein $R_1$ is

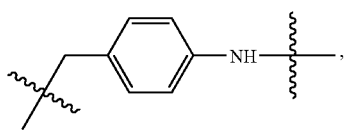

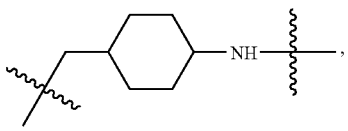

or

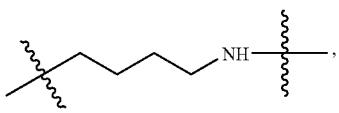

and $R_2$ is H, methyl, ethyl, or propyl.

L is a metal cation or analyte-specific moiety and i is not less than one and i equals or is less than n−1.

For the polymers contained in the magnetic resonance imaging contrast agent in the embodiments, P can be any conventional binding segment of ethylene glycol and its derivatives, preferably polymer segments of poly ethylene glycol. In some embodiments, D is a $C_{3-30}$ dendritic moiety with n oxygen residual groups which can be bonded with D and a plurality of Z. Preferably, D is 2,2-dihydroxymethyl propanoic acid and residual groups of the derivative thereof, such as

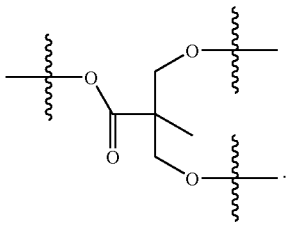

Additionally, D can be a dendrimer moiety with layers of unrestricted numbers, preferably 2 to 3 layers, such as

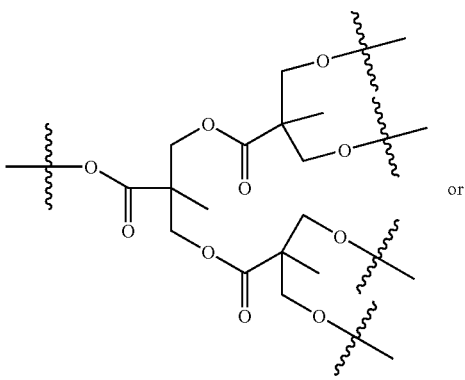

or

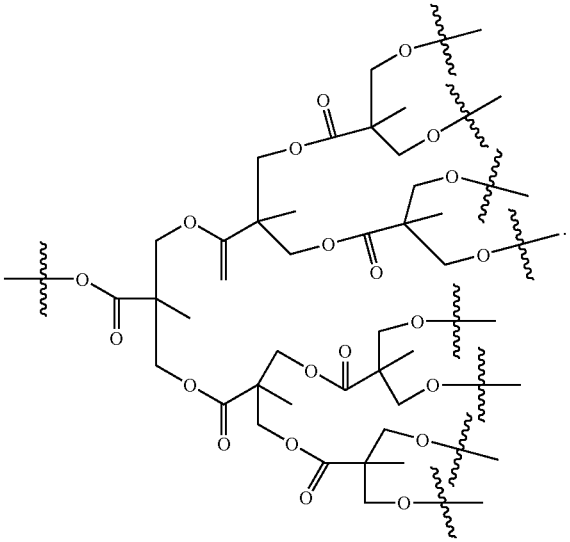

The metal cation in some embodiments is capable of taking part in the physiological metabolism as a developing agent with high sensitivity and precision of magnetic resonance, such as $Gd^{3+}$. According to some embodiments, the analyte-specific moiety is a molecular moiety specifically reacting with a specific target, such as a folic acid group, a glucose group, or an amino acid group. In some embodiments, Z can be a chelated agent, such as a residual group of ethylenedinitrilo tetraacetic acid (EDTA) or a residual group of ethylenediimino dibyric acid (EDBA). In addition, Z can be

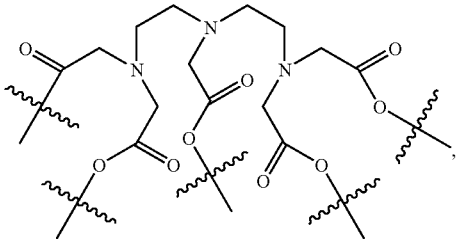

wherein Z bonds with D by one oxygen atom and bonds with L by the other oxygen atoms.

Further, the magnetic resonance imaging contrast agent can be a water soluble star-shaped dendritic polymer.

A detailed description is given in the following embodiments with reference to the accompanying drawings.

DETAILED DESCRIPTION OF THE INVENTION

The following description is of the best-contemplated mode of carrying out the invention. This description is made for the purpose of illustrating the general principles of the invention and should not be taken in a limiting sense. The invention provides a dendritic polymer and a magnetic resonance imaging contrast agent, employing the dendritic polymer, capable of recognizing an affected part of a human body with high sensitivity. Although the invention is described with respect to a specific embodiment, the principles of the invention, as defined by the claims appended herein, can obviously be applied beyond the specifically described embodiments of the invention described herein. Moreover, in the description

EXAMPLE 1
Preparation of Dendritic Polymer (A) S–(P-$D_1$–(Z-Gd)$_2$)$_5$ Containing Metal Cation $Gd^{3+}$
S:
$D_1$:
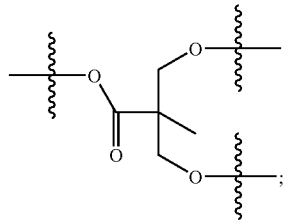
Z:
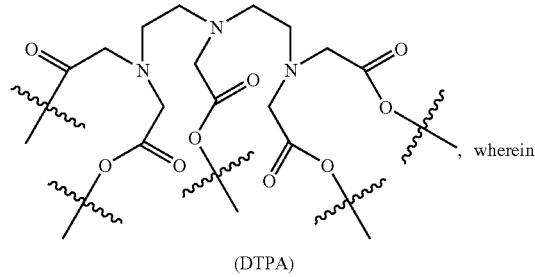
, wherein
(DTPA)
P: polyethylene glycol segment (molecular weight ~2000)
$D_1$ bonds with a carbonyl group (CO) of DTPA by an oxygen residual group to form an ester group (COO).
Preparation procedure of the polymer (A) is shown as below:
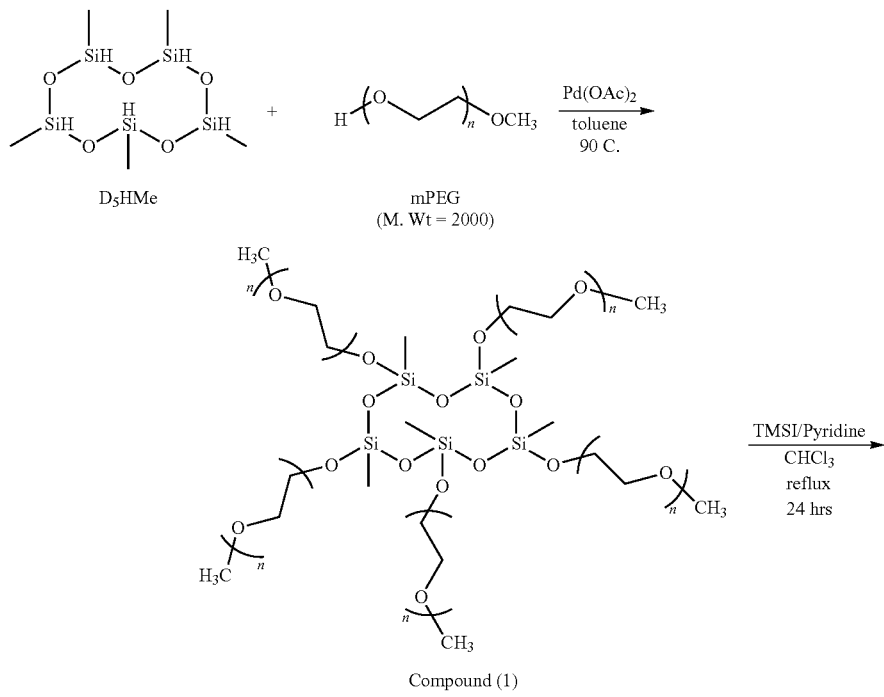
Compound (1)

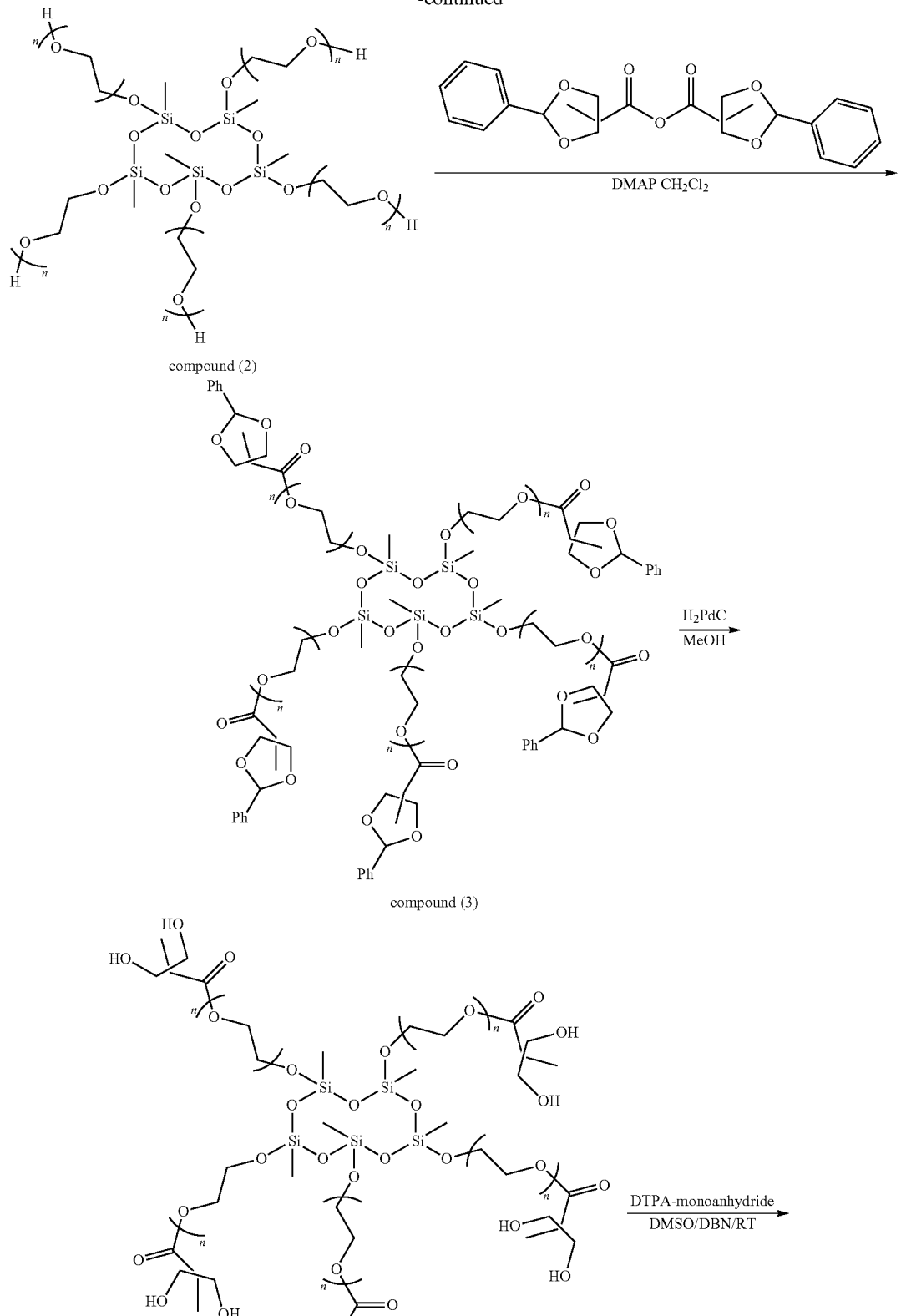

Polymer (A)

mPEG (16.63 g, 8.32 mmol) was degassed for an hour at 90° C. Toluene (10 mL) was added and then Pd(OAc)$_2$ (0.056 g, 3 mol % with respect to mPEG) was added followed by 2,4,6,8,10-pentamethylcyclopentasiloxane (D$_5$HMe) (0.5 g, 1.66 mmol). The reaction mixture was then stirred at 90° C. for 48 hours, diluted with dichloromethane (500 mL) and filtered through Celite 545. The filtrate was concentrated and dried to afford the compound (1) (2,4,6,8,10-pentamethylcyclopentasiloxane-pentamethoxypolyethylene glycol, D$_5$-Me-(PEG-OMe)$_5$). Physical measurement of the compound (1) is listed below:

$^1$HNMR (CDCl$_3$, 400 MHz): δ 0.13 (s, 15H, —Si—CH3), 3.36 (s, 15H, —OCH3), 3.63 (bs).

A two necked R.B flask was charged with compound (1) (D$_5$-Me-(PEG-OMe)5) (8.0 g, 0.78 mmol) and one neck was fitted with a reflux condenser through which nitrogen was purged and the other neck was sealed with a rubber septum. Chloroform (10 mL), pyridine (0.12 g, 1.52 mmol) and iodotrimethylsilane (TMSI) (1.67 g, 5.83 mmol) were consequently injected. When iodotrimethylsilane was added, the reaction mixture became yellow in colour. Then, the reaction mixture was heated at 50° C., without stirring, for 24 hours. After 24 hours, anhydrous methanol was added to quench the reaction, and the reaction mixture was stirred for an additional 30 minutes. Then, the contents of the flask were poured into a beaker containing excess of diethyl ether. The ether layer was separated and concentrated to give the compound (2) (2,4,6,8,10-pentamethylcyclopentasiloxane-pentahydroxy(terminal) polyethylene glycol, D$_5$-Me-(PEG-OH)$_5$) as a viscous liquid. Physical measurement of the compound (2) is listed below:

$^1$HNMR (CDCl$_3$, 400 MHz): δ 0.08 (s, 15H, —Si—CH3), 3.64 (bs).

A mixture of compound (2) (D$_5$-Me-(PEG-OH)$_5$) (5.0 g, 0.49 mmol), 4-dimethylaminopyridine (DMAP) (0.12 g, 0.98 mmol) and benzylidene-2,2'-bis(oxy)methylpropionic anhydride (3.12 g, 7.32 mmol) in dichloromethane (200 mL) was stirred at room temperature 36 hours. Methanol was added and the stirring was continued for another 12 hours in order to quench the excess of BOP anhydride. Then the solvent was completely removed and the residue was added to diethyl ether (1 L). The viscous material was separated and dried to give the compound (3) (D$_5$-Me-PEG-(O2Bn)$_5$). Physical measurement of the compound (3) is listed below:

$^1$HNMR (CDCl$_3$, 400 MHz): δ 0.12 (s, 15H, —Si—CH3), 1.13 (s, 15H, —CH3), 3.59-3.80 (m), 4.66 (m), 5.48 (s, 5H, benzylidene CH), 7.34 (m, 15H, Ar—H), 7.46 (m, 10H, Ar—H).

To a mixture of compound (3) (D$_5$-Me-[PEG-G1-(O2Bn)$_2$]$_5$) (3.0 g, 0.27 mmol) and Pd/C (10%) (0.2 g) in methanol (150 mL), H$_2$ gas was flushed for 32 hours with stirring. Then, the catalyst was filtered through Celite and the filtrate was concentrated. Chloroform (50 mL) was added to the mixture, the separated solid was filtered off and dried to obtain the compound (4) (D$_5$-Me-PEG-G$_1$-(OH)$_{10}$). Physical measurement of the compound (4) is listed below:

$^1$HNMR (CDCl$_3$, 400 MHz): δ 0.10 (s, 15H, —Si—CH3), 1.02 (s, 15H, —CH3), 3.21-3.88 (bm), 12.06 (bs, —OH).

To a solution of compound (4) (D$_5$-Me-PEG-G1-(OH)$_{10}$) (2.0 g, 0.19 mmol) in DMSO (10 mL) triethylamine (0.37 g, 3.70 mmol) was added and the reaction mixture was stirred for 10 minutes. Then, a solution of DTPA monoanhydride (1.39 g, 3.70 mmol) in DMSO (100 mL) was added dropwise and the reaction mixture was stirred at room temperature for 48 hours. The solvent was partially removed, dialysed against DI water and freeze-dried to afford the compound (5) (D$_5$-Me-PEG-G1-(ODTPA)$_{10}$). Physical measurement of the compound (5) is listed below:

$^1$HNMR (CDCl$_3$, 400 MHz): δ 0.07 (s, 15H, —Si—CH3), 1.12 (s, 15H, —CH3), 2.98-3.94 (bm), 4.26 (m).

Finally, a mixture of compound (5) (0.517 g, 0.04 mmol) and Gd$_2$O$_3$ (0.0644 g, 0.18 mmol) was dissolved in DI water and the reaction mixture was heated at 60° C. for 20 hours. Then, it was cooled to room temperature and filtered through 0.2 μm filter paper and freeze-dried to furnish dendritic polymer (A) S-(P-D$_1$-(Z—Gd)$_2$)$_5$ containing metal cation Gd$^{3+}$ as a yellow solid.

EXAMPLE 2

Preparation of Dendritic Polymer (B) Containing Metal Cation Gd$^{3+}$

S:

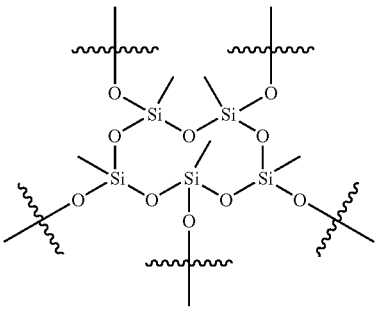

P: polyethylene glycol segment (molecular weight ~2000):

D$_2$:

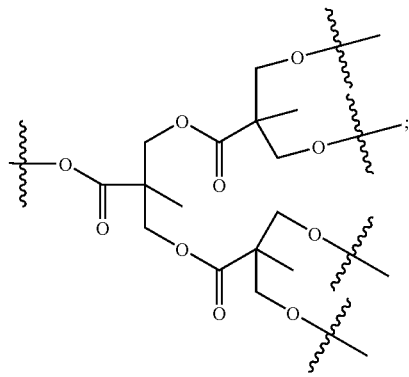

Z:
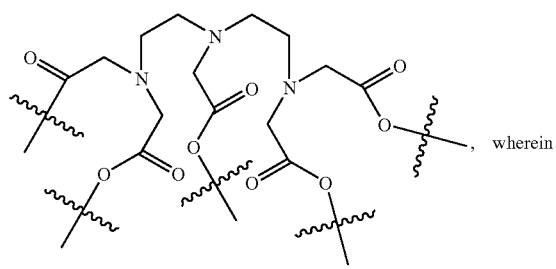
(DTPA)
, wherein
$D_2$ bonds with a carbonyl group (CO) of DTPA by an oxygen residual group to form an ester group (COO)
Preparation procedure of the polymer (B) is shown as below:
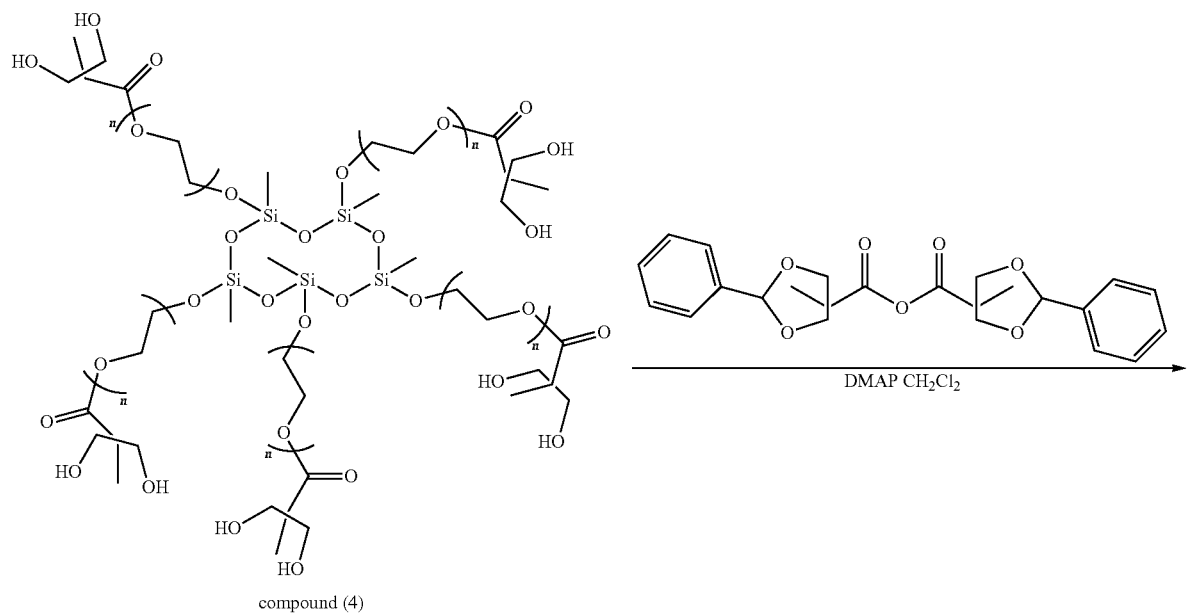
compound (4)
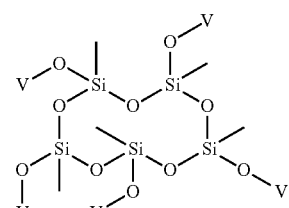
compound (6)

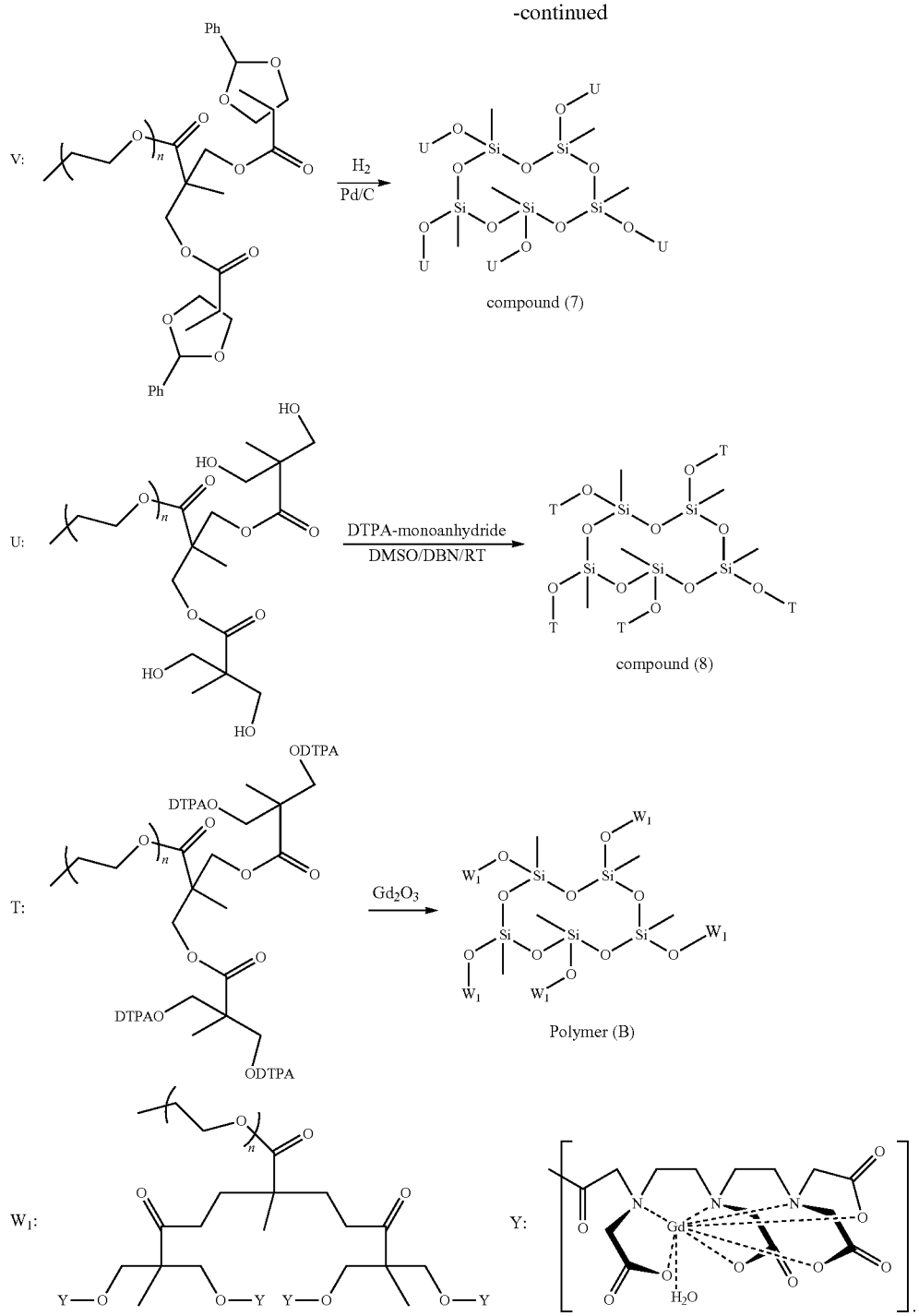

A solution of benzylidene-2,2'-bis(oxy)methylpropionic anhydride (3.12 g, 7.32 mmol) in dichloromethane (150 mL) was added to a mixture of compound (4) ($D_5$-Me-PEG-G1-$(OH)_{10}$) (4.0 g, 0.37 mmol) and 4-dimethylaminopyridine (DMAP) (0.090 g, 0.74 mmol) in dichloromethane (50 mL) and the reaction mixture was stirred at room temperature for 48 hours. Then, methanol (20 mL) was added and the stirring was continued for another 10 hours in order to quench the reaction. Then the solvent was completely removed and the again methanol was added. The separated solid was filtered and the filtrate was added dropwise to a beaker containing diethyl ether (1 L). The viscous material was separated and dried to give the compound (6) ($D_5$-Me-PEG-G1-$(O_2Bn)_{10}$) in 59% yield. Physical measurement of the compound (6) is listed below:

$^1$HNMR ($CDCl_3$, 400 MHz): δ 1.03 (s, 15H), 1.06 (s, 30H), 3.55-3.77 (m), 5.44 (s, 10H, benzylidene CH), 7.29-7.42 (m, 50H, Ar—H).

To a mixture of compound (6) ($D_5$-Me-PEG-G1-$(O_2Bn)_{10}$) (2.5 g, 0.20 mmol) and Pd/C (10%) (0.2 g) in methanol (100 mL), $H_2$ gas was flushed for 48 hours with stirring. Then, the catalyst was filtered through Celite and the filtrate was precipitated by adding dropwise to a large excess of diethyl ether, obtaining a compound (7) ($D_5$-Me-PEG-$G_2$-$(OH)_{20}$). Physical measurement of the compound (7) is listed below:

$^1$HNMR ($CDCl_3$, 400 MHz): δ 0.92 (s, 15H), 0.98 (s, 30H), 3.08 (s), 3.40-3.77 (m).

To a solution of compound (7) ($D_5$-Me-PEG-$G_2$-$(OH)_{20}$) (2.0 g, 0.17 mmol) in DMSO (20 mL) 1,5-diazabicyclo[4.3.0]non-5-ene (DBN) (0.42 g, 3.34 mmol) was added and the reaction mixture was stirred for 10 minutes. Then, a solution of DTPA monoanhydride (2.51 g, 6.68 mmol) in DMSO (130 mL) was added dropwise and the reaction mixture was stirred at room temperature for 3 days. Then, the reaction mixture was dialysed against DI water and freeze-dried to afford the compound (8) ($D_5$-Me-PEG-$G_2$-$(ODTPA)_{20}$) in 29% compound. Physical measurement of the compound (8) is listed below:

$^1$HNMR ($CDCl_3$, 400 MHz): δ 0.1.19 (s) 1.22 (s), 3.16-3.875 (m).

A mixture of compound (8) ($D_5$-Me-PEG-$G_2$-$(ODTPA)_{15}$) (0.5050 g, 0.029 mmol) and $Gd_2O_3$ (0.0753 g, 0.20 mmol) was dissolved in DI water (40 mL) and the reaction mixture was heated at 70° C. for 20 hours. The reaction mixture was cooled to room temperature, filtered through 0.2 μm filter paper and then freeze-dried to furnish dendritic polymer (B) S–$(D_2$–(Z—Gd$)_4)_5$ containing metal cation $Gd^{3+}$ as a yellow solid.

EXAMPLE 3

Preparation of Dendritic Polymer (C) S–(P-$D_3$–(Z—Gd$)_8)_5$ Containing Metal Cation $Gd^{3+}$

S:

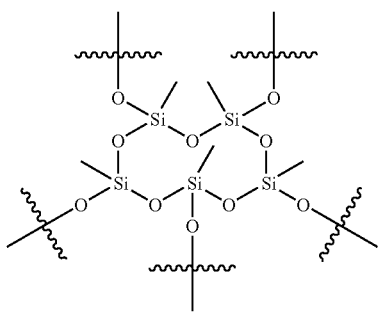

P: polyethylene glycol segment (molecular weight ~2000)

$D_3$:

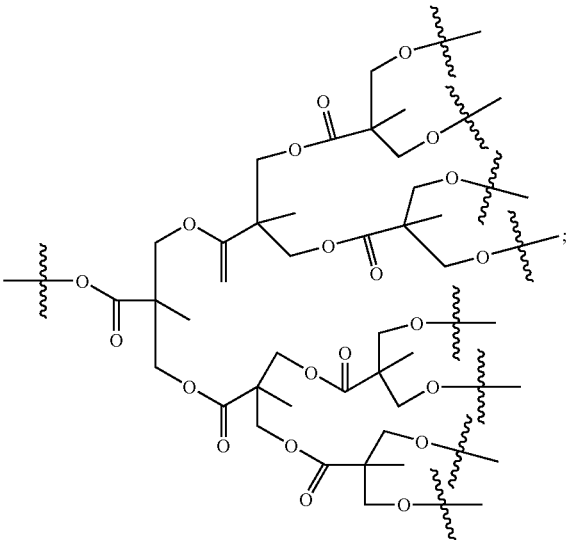

Z:

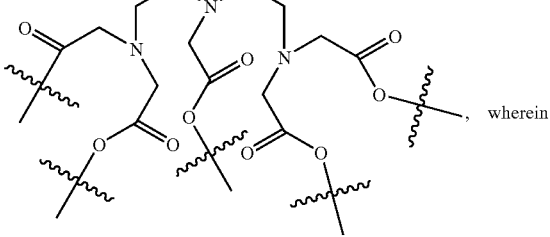

, wherein (DTPA)

$D_3$ bonds with a carbonyl group (CO) of DTPA by an oxygen residual group to form an ester group (COO).

Preparation procedure of the polymer (C) is shown as below:

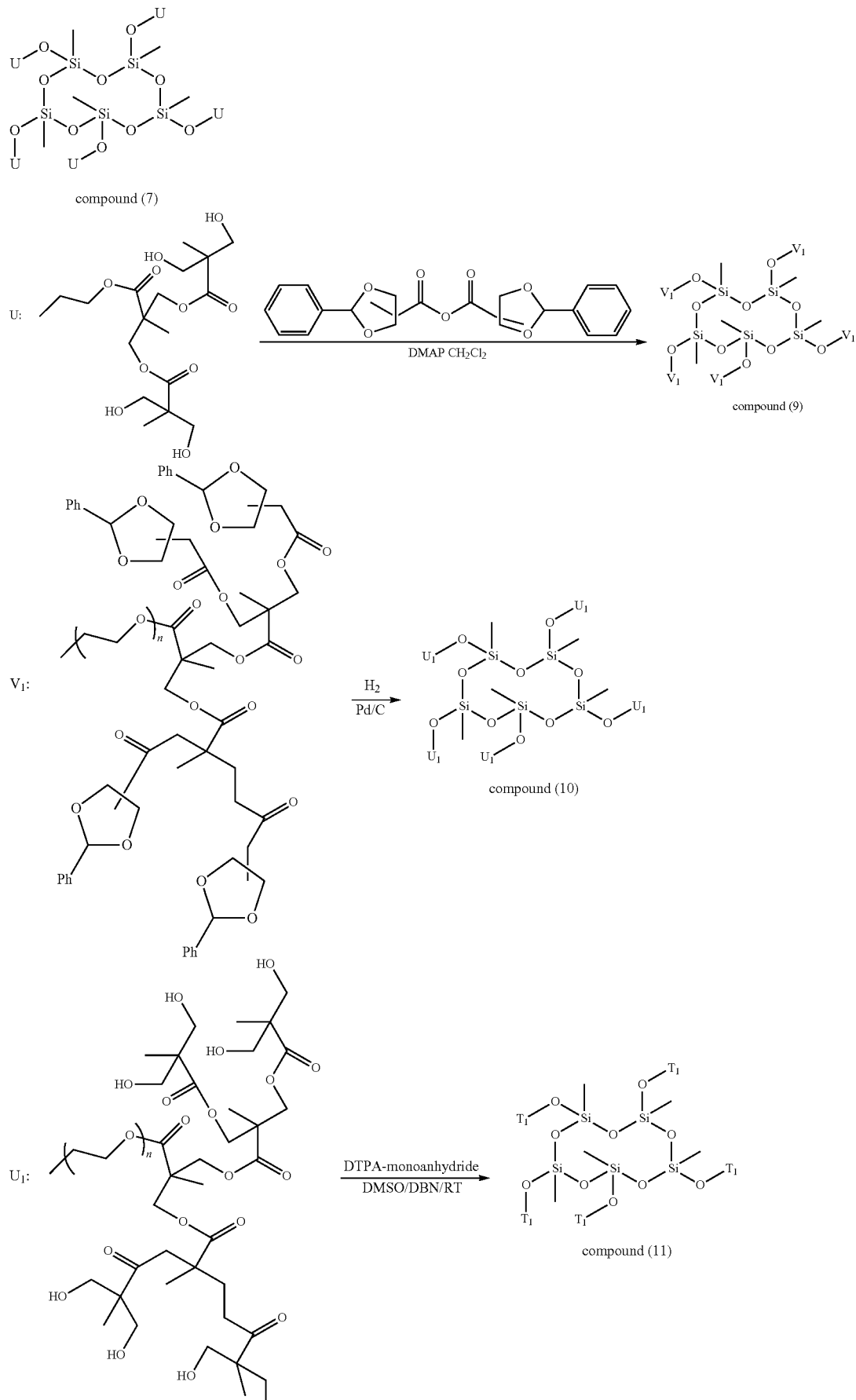

A mixture of compound (7) ($D_5$-Me-PEG-G2-(OH)20) (2.0 g, 0.17 mmol), benzylidene-2,2'-bis(oxy)methylpropionic anhydride (2.85 g, 6.70 mmol) and 4-dimethylaminopyridine (DMAP) (0.16 g, 1.33 mmol) in dichloromethane (300 mL) was stirred at room temperature for 72 hours. Then, anhydrous methanol was added and the stirring was continued for another 12 hours in order to quench the excess of BOP anhydride. The solvent was completely removed and then methanol (30 mL) was added and the separated solid was filtered and the filtrate was added to a beaker containing diethyl ether (2 L). The viscous material was separated and dried to give the compound (9) ($D_5$-Me-PEG-$G_2$-($O_2$Bn)$_{20}$) in 89% yield. Physical measurement of the compound (9) is listed below:

$^1$HNMR (CDCl$_3$, 400 MHz): δ 0.13 (s, 15H, —SiCH3), 1.02 (s, 60H), 1.05 (s, 15H), 1.10 (s, 30H), 3.04 (s), 3.57-3.78 (m), 4.56-4.66 (m), 5.44 (s, 20H, benzylidene CH), 7.31-7.34 (m, 100H, Ar—H).

Next, to a mixture of compound (9) (2.3 g, 0.14 mmol) and Pd/C (10%) (0.2 g) in a mixture of methanol (200 mL) and dichloromethane (50 mL), H$_2$ gas was flushed for 48 hours with stirring. Then, the catalyst was filtered through Celite and the filtrate was concentrated. The filtrate was added dropwise to a beaker containing diethyl ether (2 L). The viscous mass was dried to obtain the compound (10) ($D_5$-Me-PEG-$G_3$-(OH)$_{40}$).

Physical measurement of the compound (10) is listed below:

$^1$HNMR (CDCl$_3$, 400 MHz): δ 0.87 (s, 60H), 0.95 (s, 15H), 0.97 (s, 30H), 3.07 (s), 3.51-3.77 (m), 4.39-4.46 (m).

Next, to a solution of compound (10) (2.0 g, 0.14 mmol) in DMSO (20 mL) 1,5-diazabicyclo[4.3.0]non-5-ene (DBN) (1.39 g, 11.22 mmol) was added and the reaction mixture was stirred for 10 minutes. To this mixture, a solution of DTPA monoanhydride (6.31 g, 16.81 mmol) in DMSO (200 mL) was added dropwise and the reaction mixture was stirred at room temperature for 72 hours. The reaction mixture was dialysed against DI water and freeze-dried to afford the compound (11) ($D_5$-Me-PEG-$G_3$-(ODTPA)$_{40}$).

Finally, a mixture of compound (11) (0.3470 g, 0.014 mmol) and Gd$_2$O$_3$ (0.0740 g, 0.20 mmol) was dissolved in DI water (30 mL) and the reaction mixture was heated at 70° C. for 24 hours. The reaction mixture was cooled to room temperature, filtered through 0.2 μm filter paper and then freeze-dried to furnish dendritic polymer (C) S–(P-$D_3$–(Z-Hd)$_8$)$_5$ containing metal cation Gd$^{3+}$ as a yellow solid.

EXAMPLE 4

Preparation of Dendritic Polymer (C) S–(P-$D_1$–(X-$Z_1$—Gd)$_2$)$_5$ Containing Metal Cation Gd$^+$

S:

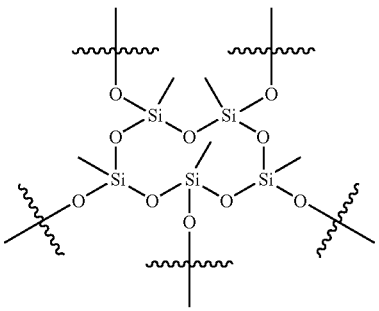

P: polyethylene glycol segment (molecular weight ~2000)

$D_1$:

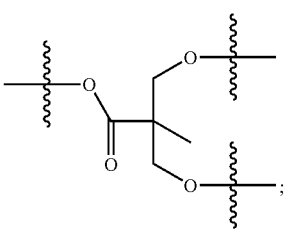

X:

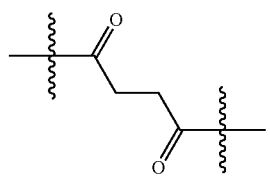

$Z_1$:

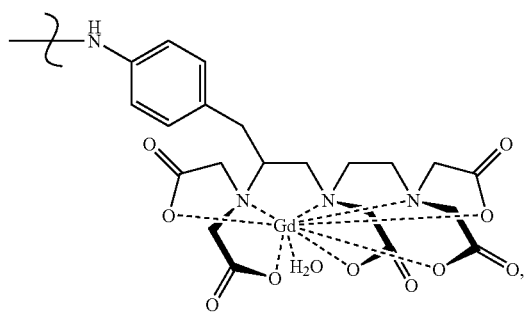

wherein $D_1$ bonds with a carbonyl group (CO) of DTPA by an oxygen residual group to form an ester group (COO).

Preparation procedure of the polymer (D) is shown as below:

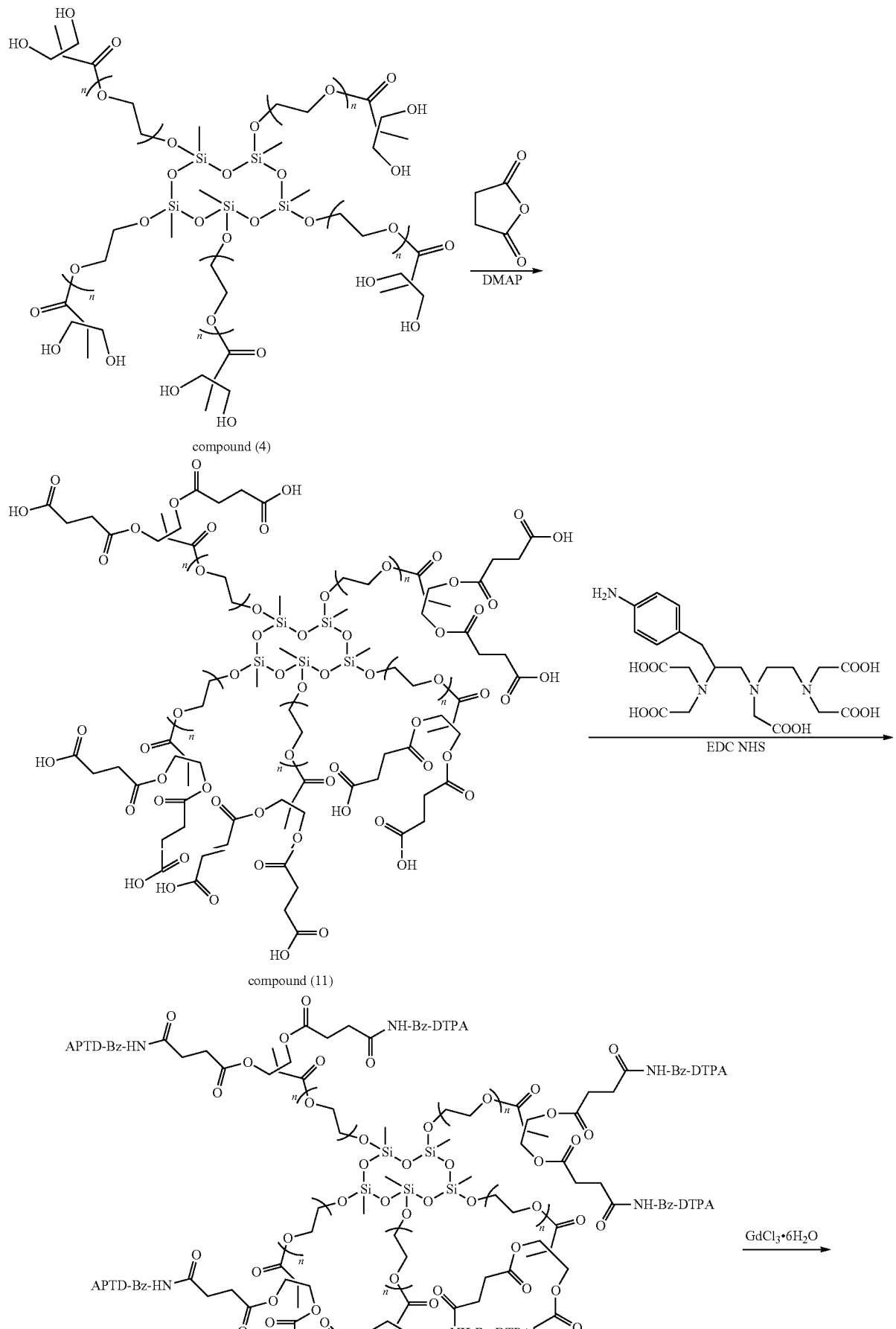

Compound (4) (1.08 g, 0.1 mmol) and DMAP (0.024 g, 0.2 mmol) were dissolved in 50 mL of dichloromethane and succinic anhydride (0.10 g, 1.0 mmol) was added. The reaction mixture was stirred overnight and the mixture was precipitated in diethyl ether (1 L). The white precipitate separated was filtered and dried under vacuum, obtaining a compound (12) ($D_5$-Me-PEG-$G_1$-$(OSA)_{10}$) with a yield 89%.

A mixture of compound (12) (0.2 g, 0.017 mmol), EDC (0.032 g, 0.20 mmol), NHS (0.024 g, 0.20 mmol) and DMAP (0.026 g, 0.20 mmol) in DMSO (10 mL) was stirred at room temperature for 2 hours and a solution of 2-(4-aminobenzyl) diethylenetriaminepentaacetic acid (0.101 g, 0.20 mmol) dissolved in 10 mL of DMSO was added dropwise with vigorous stirring. The stirring was continued for 48 hours and the reaction mixture was dialysed against DI water for about 3 days. Then the dialysed sample was lyophilized to afford the compound (13) ($D_5$-Me-PEG-$G_1$-$(NH$-$Bz$-$DTPA)_{10}$) with a yield 47%.

Finally, compound (13) (0.10 g, 0.006 mmol) was mixed with a stoichiometric amount of $GdCl_3.6H_2O$ (0.0156 g, 0.042 mmol) in water. The solution was vigorously stirred for 8 hours at room temperature. The pH was maintained at 5.8 using 0.1N NaOH solution. The progress of the reaction was followed by FTIR. The absence of free gadolinium ions were tested by using xylenol orange indicator at pH 5.8 (acetate buffer). The results were filtered using a 0.45 μm filter and lyophilized, obtaining polymer (D).

$T_1$ Relaxation Measurements

The Gadolinium loaded polymer (A)~(D) were evaluated for their capacity to alter the relaxation rate of water using an NMR spectrometer (20 MHz) with a standard pulse program of inversion-recovery (IR). The water proton relaxation results indicated that the materials have an inherent nature to act as contrast-enhancing agents. All of the three generations of cyclosiloxane-core dendrimers (polymer (A)~(C)) were analyzed and compared with a commercial contrast agent, namely, Magnevist. Generation 2 and 3 of DTPA-terminated dendrimers (polymer (B) and (C)) showed high relaxivity values, and polymer (A) of benzyl-DTPA terminated dendrimer showed much higher relaxivity values.

TABLE 1

|  | No. of DTPA/ dendrimer (Titration method) | Relaxivity (mM · s) − 1 $B_0$ = 0.47 T (molecular) | | Relaxivity/ $Gd^{3+}$ ion (ionic) | | No. of $Gd^{3+}$ ions (By ICP-AES) |
|---|---|---|---|---|---|---|
|  |  | $r_1$ | $r_2$ | $r_1$ | $r_2$ |  |
| Gd-$D_5$-Me-PEG-$G_1$-$(ODTPA)_{10}$ polymer (A) | 9.9 ± 0.1 | 70.9 | 72.4 | 7.3 | 7.5 | 9.7 |
| Gd-$D_5$-Me-PEG-$G_2$-$(ODTPA)_{20}$ polymer (B) | 15.6 ± 0.2 | 165.6 | 166.3 | 11.1 | 11.2 | 14.8 |
| Gd-$D_5$-Me-PEG-$G_3$-$(ODTPA)_{40}$ polymer (C) | 30.2 ± 0.1 | 271.6 | 287.1 | 9.3 | 9.8 | 29.3 |
| Gd-$D_5$-Me-PEG-$G_1$-$(NH$-$Bz$-$DTPA)_{10}$ polymer (D) | 7.0 | 104.6 | 109.2 | 15.2 | 15.8 | 6.9 |
| Magnevist ™ |  |  |  | 4.2 | 4.3 |  |

It should be noted that the dendritic polymers provided by the invention have an expected numbers of metal cations (for example, the expected numbers for Example 2 is 20 and the expected numbers for Example 4 is 10). However, due to the steric effect and uncertain factors from chemistry synthesis, the actual average numbers of metal cations are in general less than the expected numbers (for example, the actual average numbers of Example 2 is 15.6±0.2 and the actual average numbers of Example 4 is 7. Since dendritic polymers with different actual numbers of metal cations have various actual chemical structures, the chemical structure with the expected numbers of metal cations was used to generally represent all likely dendritic polymers with actual numbers of metal cations (which were prepared from the same synthetic process).

As shown in Table. 1, polymers (A)~(C) for Magnetic resonance imaging (MRI) were developed. It consists of paramagnetic gadolinium ions chelated to DTPA/benzyl-DTPA molecules which in turn were attached to the peripheral of the cyclic dendritic structure. The contrast enhancing properties were measured by a 20 MHz NMR spectrometer using a standard inversion recovery pulse sequence to detect the relaxation times in terms of $T_1$ and $T_2$. The relaxivities of the dendrimers were found to be much higher than commercial products. Further, the polymer (D), which had a rigid benzyl linker bridging the DTPA and the dendrimer, still exhibited superior relaxivity.

Accordingly, the disclosure introduces a concept of dendritic polymer into a design of carriers capable of carrying a plurality of paramagnetic metal cations, so as to increase the signal intensity and specific targeting ability of imaging agents per molecule. In addition, the dendritic molecule recited in the embodiments can avoid developing agents with small molecules easily breaking through the skin cells in the blood and the drawback of easy metabolism by the human body, thus increasing the time present in the blood circulation.

The invention provides five-armed cyclosiloxane based dendritic contrast agents for Magnetic resonance imaging (MRI). It consists of paramagnetic gadolinium ions chelated to DTPA (benzyl-DTPA) molecules which in turn are attached to the peripheral of the cyclic dendritic structure. These dentritic chelants can act as "magnifiers" in MRI therapy.

In addition, another technical characteristic of the disclosure is a multiple dendritic polymer carrier carrying a plurality of radioisotopes and analyte-specific moieties. Compared with conventional developing agents with large molecular carriers, such as (blood serum protein or ploy phosphoric acid), the dendritic polymers of the disclosure offer a unique magnifying ability with geometric series, so as to greatly increase signal strength of nuclear molecular imaging contrast agents per unit. The relaxivity values of the cyclosiloxane dendrimers are found to be higher due to the multiple numbers of metal cations in the cyclosiloxane dendrimers.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A dendritic polymer, comprising a structure as formula (II):

$$S\text{-}(P\text{-}D\text{-}(X\text{-}Z\text{-}L)_i)_5 \quad \text{formula (II)}$$

wherein S is

P is

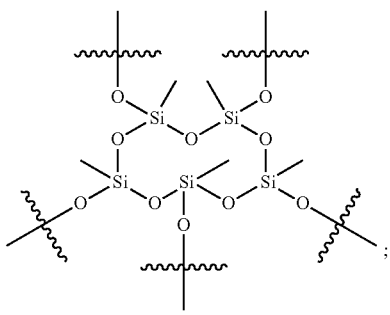

and l is not less than 1, and P bonds with S by a —CH$_2$-bond, and P bonds with D by an oxygen residual group;

D is

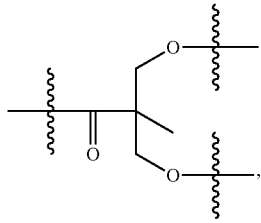

and i is 2, and D respectively bonds with X by oxygen residual groups, and D bonds with P by a

bond;

X is

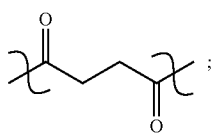

Z is a residual group of diethylene triaminepentaacetic acid or

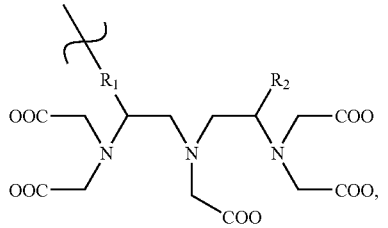, and R$_1$ is

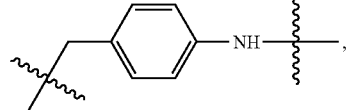,

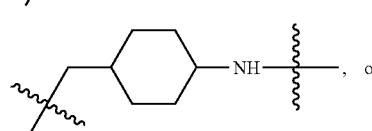, or

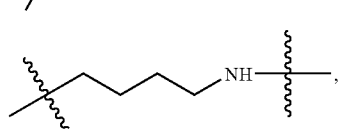, and R$_2$ is H, methyl, ethyl, or propyl; and

L is a metal cation.

2. The dendritic polymer as claimed in the claim 1, wherein the dendritic polymer is a water soluble star-shaped dendritic polymer.

3. The dendritic polymer as claimed in the claim 1, wherein L is Gd$^{3+}$.

4. The dendritic polymer as claimed in the claim 1, wherein Z comprises a metal-chelated group.

5. A magnetic resonance imaging contrast agent, comprising the dendritic polymer as claimed in the claim 1.

6. A composition comprising the dendritic polymer as claimed in claim 1 carrying a plurality of radioisotopes and analyte-specific moieties.

* * * * *